US010991455B2

(12) United States Patent
Huang et al.

(10) Patent No.: US 10,991,455 B2
(45) Date of Patent: Apr. 27, 2021

(54) AUGMENTED REALITY WITH REALTIME INTERACTIVE ANALYSIS METHOD AND SYSTEM THEREOF

(71) Applicant: DR. ADVICE CORPORATION LIMITED, Taipei (TW)

(72) Inventors: Chien-Fen Huang, Taipei (TW); Jia-Cing Lin, New Taipei (TW)

(73) Assignee: DR. ADVICE CORPORATION LIMITED, Taipei (TW)

( * ) Notice: Subject to any disclaimer, the term of this patent is extended or adjusted under 35 U.S.C. 154(b) by 442 days.

(21) Appl. No.: 16/113,980

(22) Filed: Aug. 27, 2018

(65) Prior Publication Data
US 2019/0066826 A1 Feb. 28, 2019

(30) Foreign Application Priority Data

Aug. 28, 2017 (TW) ................. 106129155

(51) Int. Cl.
| | |
|---|---|
| *G16H 10/60* | (2018.01) |
| *G06T 19/00* | (2011.01) |
| *G16H 20/60* | (2018.01) |
| *G06K 7/14* | (2006.01) |
| *G16H 50/30* | (2018.01) |
| *G06Q 50/22* | (2018.01) |
| *G16H 10/40* | (2018.01) |
| *G16H 20/30* | (2018.01) |
| *G16H 20/70* | (2018.01) |
| *G16H 40/63* | (2018.01) |

(52) U.S. Cl.
CPC ........... *G16H 10/60* (2018.01); *G06K 7/1417* (2013.01); *G06Q 50/22* (2013.01); *G06T 19/006* (2013.01); *G16H 10/40* (2018.01); *G16H 20/30* (2018.01); *G16H 20/60* (2018.01); *G16H 20/70* (2018.01); *G16H 40/63* (2018.01); *G16H 50/30* (2018.01)

(58) Field of Classification Search
CPC ........ G16H 50/20; G16H 10/60; G16H 15/00; G16H 80/00; G16H 50/30; G16H 50/70; A61B 5/744
See application file for complete search history.

(56) References Cited

U.S. PATENT DOCUMENTS

| | | | | |
|---|---|---|---|---|
| 2012/0165618 | A1* | 6/2012 | Algoo | G16H 50/20 600/300 |
| 2017/0229149 | A1* | 8/2017 | Rothschild | G16H 40/63 |
| 2018/0114595 | A1* | 4/2018 | Stern | H04L 67/1004 |

* cited by examiner

*Primary Examiner* — Joseph D Burgess
(74) *Attorney, Agent, or Firm* — Procopio, Cory, Hargreaves & Savitch LLP

(57) ABSTRACT

An augmented reality with real-time interactive analysis method and a system thereof are provided. The method includes: starting an application from a portable electronic device by a user; reading a checklist by the application; identifying basic data fields and biochemical fields of the checklist; recording the basic data fields and the data in the biochemical fields and converting them into digital data; determining whether the data of the biochemical fields meets a preset standard value; according to whether the results conform to the preset standard value, the application produces correspondingly a first signal or a second signal; the application generating an augmented reality checklist image and adding a signal field to each biochemical field; and displaying the first signal or the second signal corresponding to the biochemical fields in the signal field; wherein each preset standard value is pre-stored in the application.

9 Claims, 6 Drawing Sheets

AUGMENTED REALITY WITH REALTIME INTERACTIVE ANALYSIS METHOD AND SYSTEM THEREOF

CROSS REFERENCE TO RELATED APPLICATION

This U.S. patent application is based on and claims the benefit priority from Taiwanese Patent Application No. 106129155, filed on Aug. 28, 2017, the disclosure of which is hereby incorporated by reference herein in its entirety.

BACKGROUND

1. Technical Field

The present disclosure relates to an augmented reality with real-time interactive analysis method and a system thereof, in particular, to an augmented reality with real-time interactive analysis method and a system thereof achieved by means of a portable electronic device and a checklist or a portable electronic device and a biochemical checklist.

2. Description of Related Art

The existing checklists such as a health checklist, a biochemical checklist, and so on, are displayed in the form of word document and incapable of providing interactive modes for readers, thus resulting in that the conventional checklists demonstrated in a verbal form cannot be applied in an animated and interactive manner to readers.

SUMMARY

The present disclosure is related to an augmented reality with real-time interactive analysis method and a system thereof. In practice, the present disclosure can be installed in a smart phone or a tablet, and by virtue of the present disclosure, users can read a health checklist or a biochemical checklist in an animated and interactive manner. Consequently, the present disclosure can effectively stimulate users to use applications installed in the smart handheld device and overcome the drawbacks associated with conventional checklists.

The present disclosure provides augmented reality with real-time interactive analysis method applicable to a portable electronic device, wherein the augmented reality with real-time interactive analysis method is an application installed in the portable electronic device, and wherein the portable electronic device comprises a display screen, the application interacts with a checklist, and wherein the checklist comprises a plurality of basic data fields and a plurality of biochemical fields; the augmented reality with real-time interactive analysis method comprising the steps of: starting the application from the portable electronic device by a user; reading the checklist by the application; identifying the plurality of basic data fields of the checklist and the plurality of biochemical fields of the checklist; recording the plurality of basic data fields and data in the plurality of biochemical fields and converting the plurality of basic data fields and data in the plurality of biochemical fields into digital data; determining whether the data of each of the plurality of biochemical fields meets a preset standard value, and wherein each biochemical field corresponds to a preset standard value; the application producing a first signal or a second signal corresponding to whether results conform to the preset standard values; the application generating an augmented reality checklist image and adding a signal field to each of the plurality of biochemical fields; and displaying the first signal or the second signal corresponding to the plurality of biochemical fields in the signal field; wherein each of the preset standard values is pre-stored in the application.

DESCRIPTION OF THE EXEMPLARY EMBODIMENTS

Figure 1:
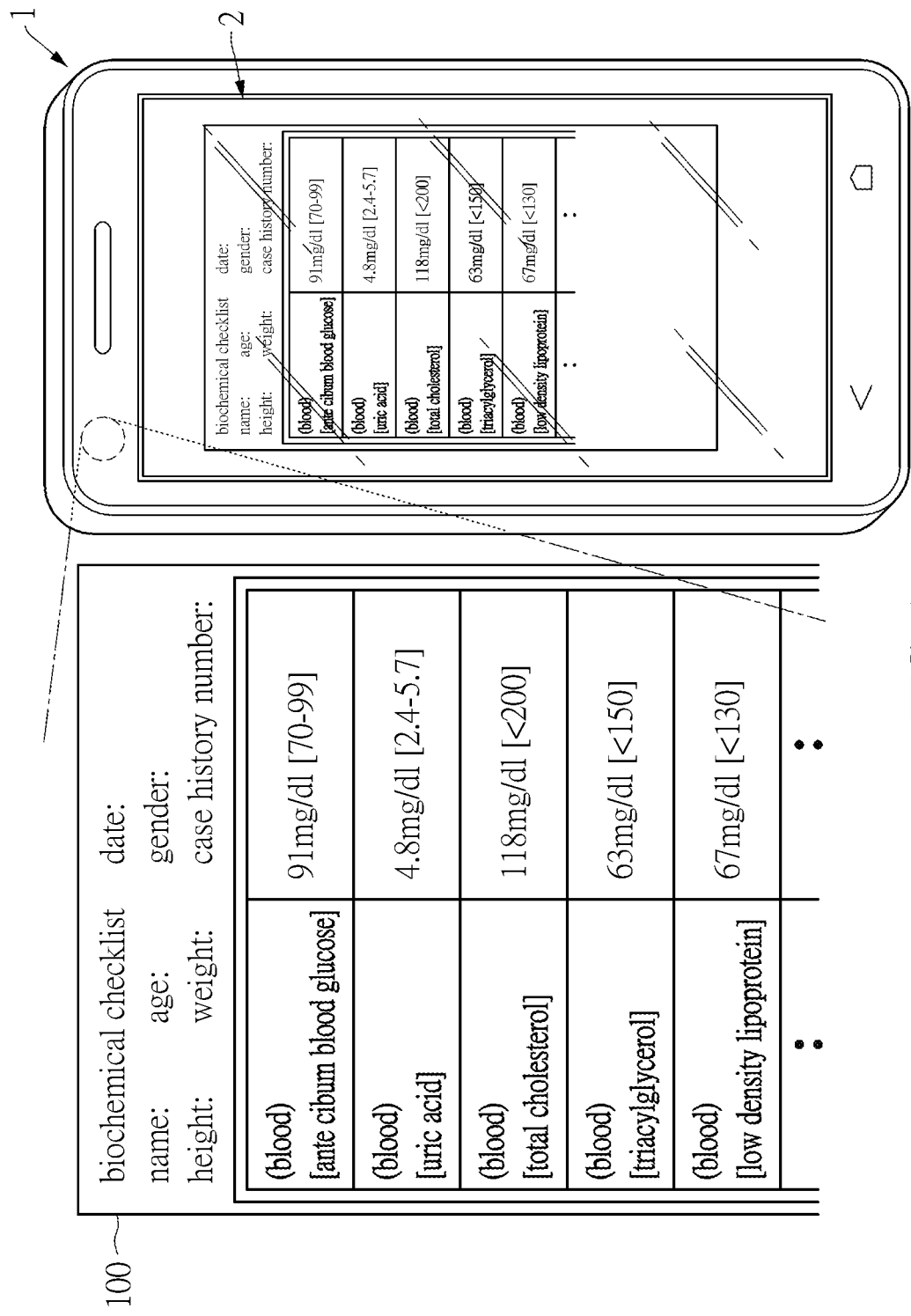
FIG. 1 is a schematic diagram of the operation according to an embodiment of the present disclosure.

Reference will now be made in detail to the exemplary embodiments of the present disclosure, examples of which are illustrated in the accompanying drawings. Wherever possible, the same reference numbers are used in the drawings and the description to refer to the same or like parts.

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a," "an" and "the" and exemplary steps "S00", "S01", and so on are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Referring to FIG. 1, an exemplary aspect of an augmented reality with real-time interactive analysis method and a system thereof provided by the present disclosure before being used is shown. The augmented reality with real-time interactive analysis method of the present disclosure can be disposed in a portable electronic device 1, meaning that the augmented reality with real-time interactive analysis method of the present disclosure is installed in the portable electronic device 1. The portable electronic device 1 can be a smart phone, a tablet or a smart watch. The portable electronic device 1 is disposed with a display screen 2 and can interact with a checklist 100. In practice, the checklist 100 can be a personal health checklist, a biochemical checklist, or a physical examination report, and includes a plurality of basic data fields and a plurality of biochemical fields. As shown in FIG. 1, the plurality of basic data fields include items such as date, name, age, gender, height, weight, case history number, and so on, and the plurality of biochemical fields include (blood) ante cibum blood glucose, (blood) uric acid, (blood) total cholesterol, (blood) triacylglycerol, (blood) low density lipoprotein, and so on. In addition, the numerical values corresponding to the plurality of biochemical fields are respectively displayed at the right side of each of the plurality of biochemical fields.

Further, the augmented reality with real-time interactive analysis method provided by the present disclosure can be an application installed in the portable electronic device 1, and the application is commonly demonstrated in a mode of an APP. In practice, the augmented reality with real-time interactive analysis method of the present disclosure employs an APP to provide an augmented reality with real-time interactive analysis and display the necessary augmented reality image on the display screen 2 of the portable electronic device 1.

Figure 2:
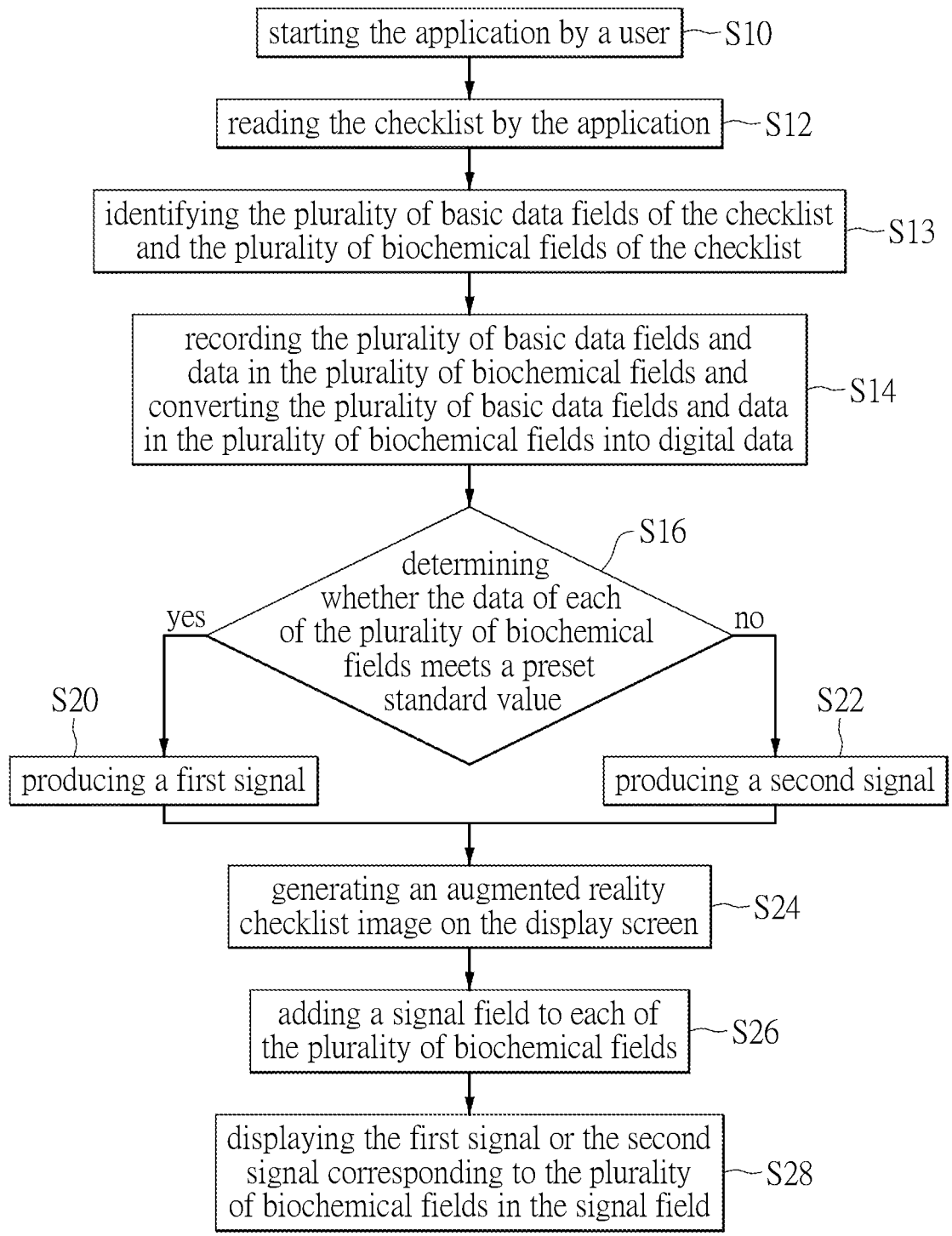
FIG. 2 is a flow chart of the augmented reality with real-time interactive analysis method according to an embodiment of the present disclosure.
Figure 5:
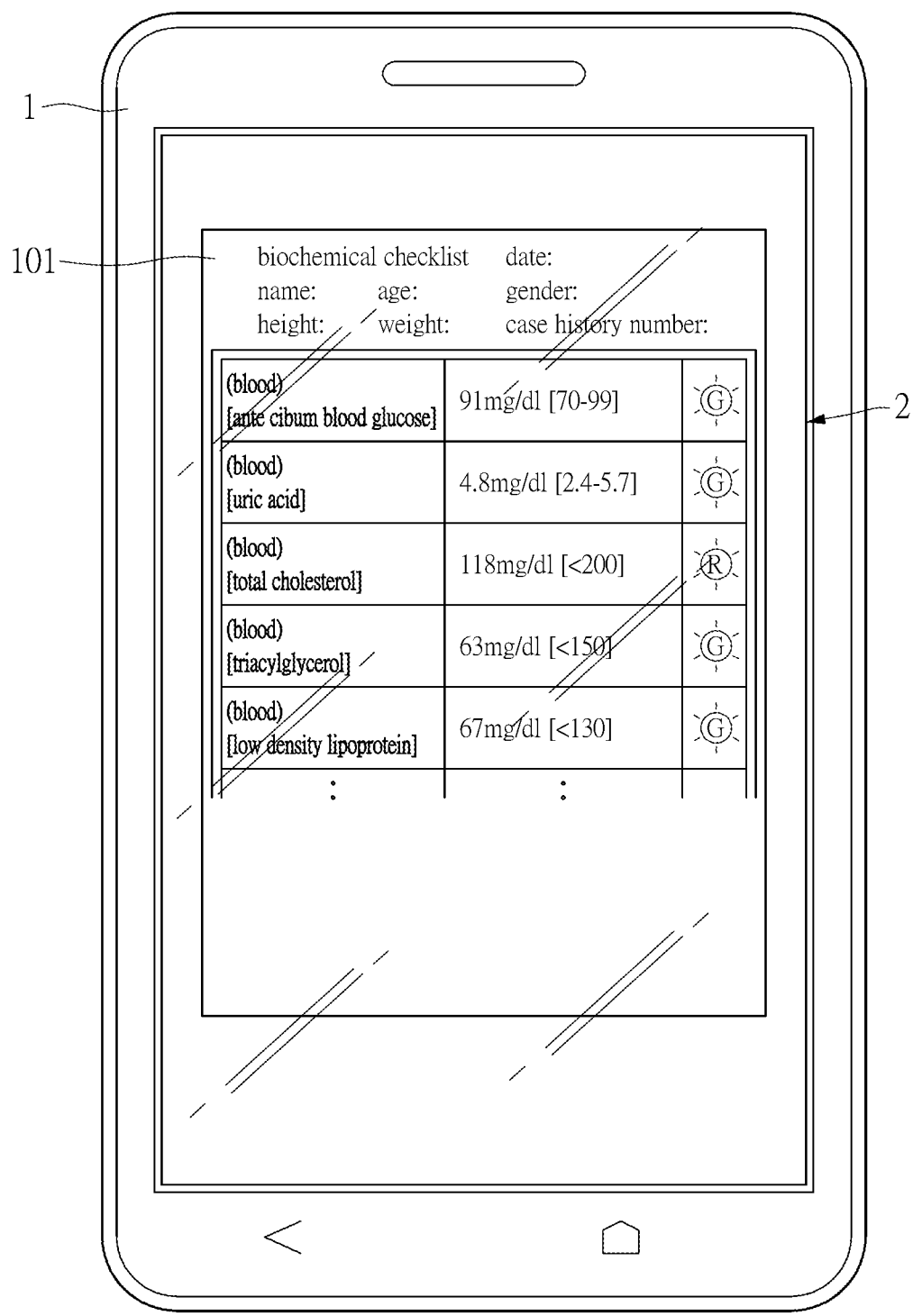
FIG. 5 is a schematic diagram of an augmented reality image according to an embodiment of the present disclosure.

FIG. 2 is a flow chart of the augmented reality with real-time interactive analysis method according to an embodiment of the present disclosure. The steps include: S10: starting the application by a user; S12: reading the checklist by the application; S13: identifying the plurality of basic data fields of the checklist and the plurality of biochemical fields of the checklist; S14: recording the plurality of basic data fields and data in the plurality of biochemical fields and converting the plurality of basic data fields and data in the plurality of biochemical fields into digital data; S16: determining whether the data of each of the plurality of biochemical fields meets a preset standard value, and wherein each biochemical field corresponds to a preset standard value; S20: the application producing a first signal corresponding to whether results conform to the preset standard values; S22: the application producing a second signal corresponding to whether results conform to the preset standard values; S24: the application generating an augmented reality checklist image 101 (as shown in FIG. 5) on the display screen; S26: adding a signal field to each of the plurality of biochemical fields; and S28: displaying the first signal (e.g. a green light (G)) or the second signal (e.g. a red light (R)) corresponding to the plurality of biochemical fields in the signal field (as shown in FIG. 5). In S16, each of the preset standard values is pre-stored in the application, that is, the preset standard values respectively corresponding to the plurality of biochemical fields are stored in the APP in advance.

Specifically, the preset standard values pre-stored in the augmented reality with real-time interactive analysis method of the present disclosure can be respectively a preset standard value/interval. For example, <200 mg/dl is set as the preset standard value of total cholesterol, 70-99 mg/dl is set as the preset standard interval of ante cibum blood glucose, 2.4-5.7 mg/dl is set as the preset standard interval of uric acid, <150 mg/dl is set as the preset standard value of triacylglycerol, and <130 mg/dl is set as the preset standard value of low density lipoprotein. Each preset standard value/interval mentioned above is used as an exemplary example, and the present disclosure is not limited thereto. The preset standard value and the preset standard interval can be made according to practical requirements.

In the exemplary aspect, if the data of each of the plurality of biochemical fields meets a preset standard value, a first signal is produced by the application; if the data of each of the plurality of biochemical fields exceeds a preset standard value, a second signal is produced by the application; if the data of each of the plurality of biochemical fields falls behind a preset standard value, a third signal is produced by the application; and the first, second and third signals corresponding to each of the plurality of biochemical fields are respectively displayed on a signal field of each of the plurality of biochemical fields. That is, after determining the data of each of the plurality of biochemical fields, the present disclosure provides signals according to the determination. The first signal can be a green light (G), the second signal can be a red light (R), and the third signal can be a yellow light (Y), but the present disclosure is not limited thereto. In practice, the first, second and third signals can be a blue light, a pinky light and a purple light respectively, or a black light, a white light and a grey light respectively. Briefly, the signals provided by the present disclosure can be lights with various colors which correspond to different healthy conditions respectively.

Figure 6:
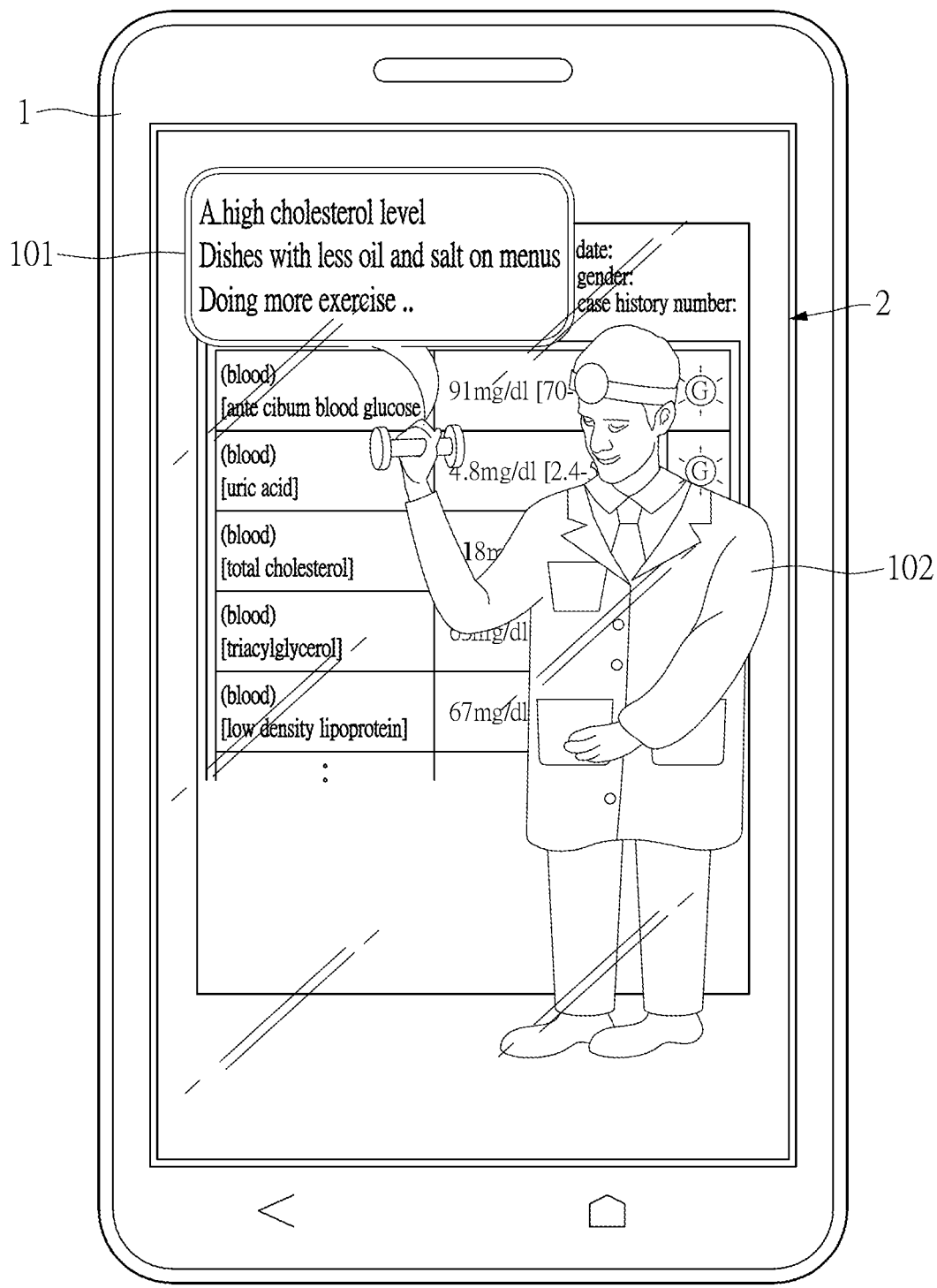
FIG. 6 is a schematic diagram of an augmented reality image of a doll and a dialog box according to an embodiment of the present disclosure.

In addition to the application of the first and second signals, after S16, the augmented reality with real-time interactive analysis method of the present disclosure further includes that the application further obtains a biochemical field from each of the plurality of biochemical fields which does not mostly comply with the preset standard value, and produces and displays an augmented reality image of a doll and a dialog box 102 on the display screen 2 as shown in FIG. 6. In FIG. 6, the augmented reality image of a doll and a dialog box 102 covers partially the augmented reality checklist image 101. That is to say, in addition to the display of a green light and a red light, an augmented reality image of a doll and a dialog box 102 is also applied and displayed on the display screen 2 of the portable electronic device 1.

Figure 3:
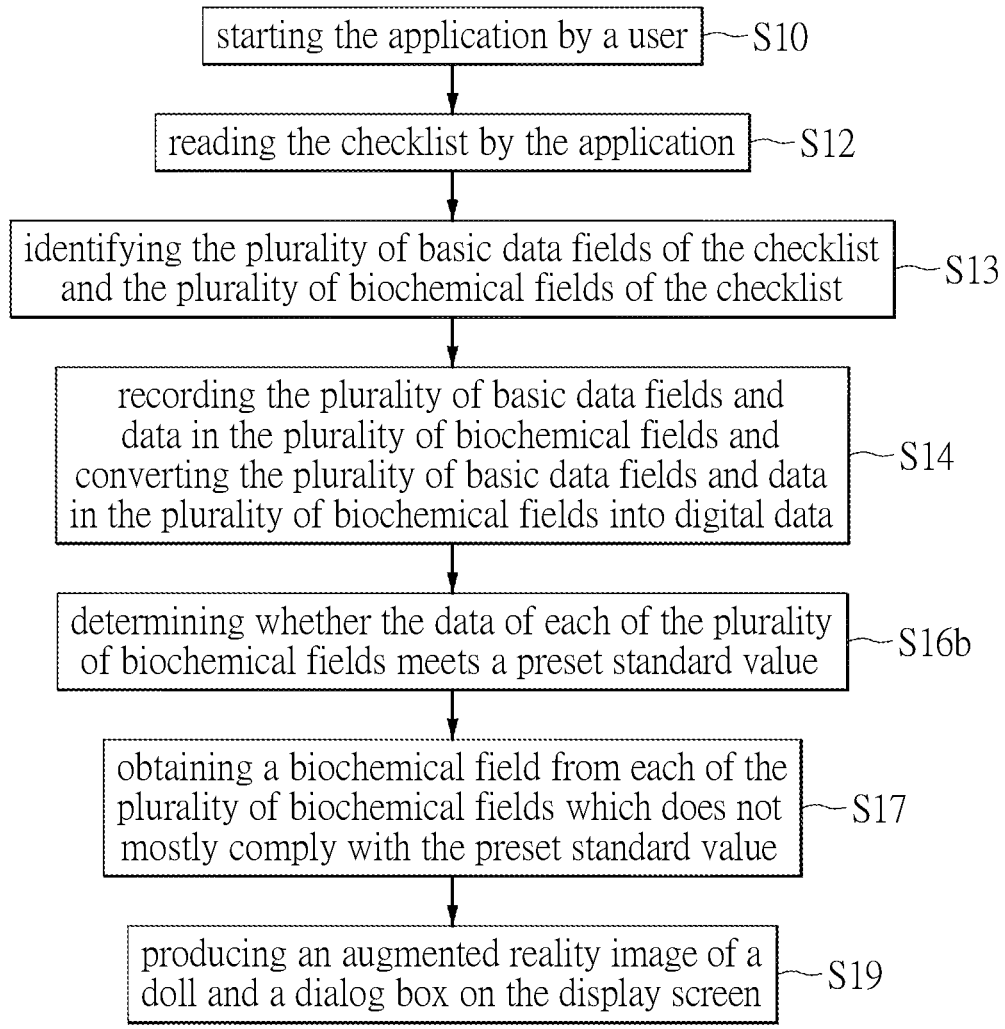
FIG. 3 is a flow chart of the augmented reality with real-time interactive analysis method according to another embodiment of the present disclosure.

Reference is made FIG. 3, which is a flow chart of the augmented reality with real-time interactive analysis method according to another embodiment of the present disclosure. In the present embodiment, the augmented reality image of a doll and a dialog box 102 is applied without considering the exemplary aspect of the first signal, the second signal and the third signal. The present embodiment is also applicable to the portable electronic device 1, and the augmented reality with real-time interactive analysis method applied to the present embodiment is an application installed in the portable electronic device 1, in which the application is the so-called APP. The portable electronic device 1 is disposed with a display screen 2, and the application interacts with a checklist 100. The checklist 100 includes a plurality of basic data fields and a plurality of biochemical fields.

The augmented reality with real-time interactive analysis method according to another embodiment of the present disclosure includes: S10: starting the application by a user; S12: reading the checklist by the application; S13: identifying the plurality of basic data fields of the checklist and the plurality of biochemical fields of the checklist; S14: recording the plurality of basic data fields and data in the plurality of biochemical fields and converting the plurality of basic data fields and data in the plurality of biochemical fields into digital data; S16*b*: determining whether the data of each of the plurality of biochemical fields meets a preset standard value, and wherein each biochemical field corresponds to a preset standard value; S17: obtaining a biochemical field from each of the plurality of biochemical fields which does not mostly comply with the preset standard value, and the application generating an augmented reality checklist image 101 on the display screen 2, and S19: producing an augmented reality image of a doll and a dialog box 102 on the display screen 2, in which the augmented reality image of a doll and a dialog box 102 covers partially the display screen 2. The content of the augmented reality image of a doll and a dialog box 102 is suggestions and prompting associated with the data in the biochemical field which does not mostly comply with the preset standard value.

As shown in FIG. 6, the doll of the augmented reality image is demonstrated as a doctor for an exemplary aspect, and the content of the dialog box, which is the suggestions about the data of total cholesterol in the biochemical field, displays a high cholesterol level, dishes with less oil and salt on menus, doing more exercise, and so on. In practice, the doll can be a doctor or a nurse, and the present disclosure is not limited thereto.

Figure 4:
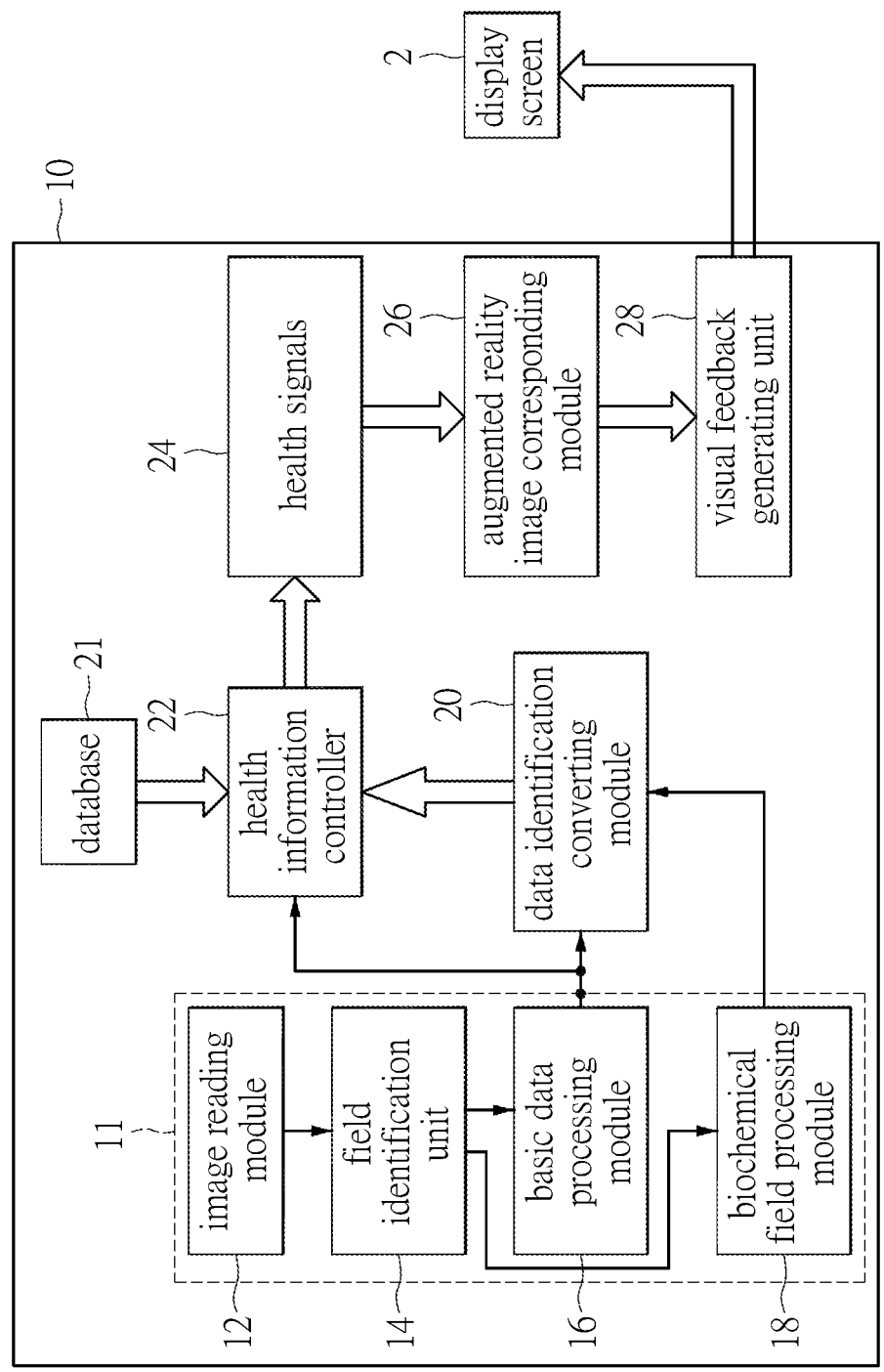
FIG. 4 is a block diagram of the interior of the augmented reality with real-time interactive analysis system according to an embodiment of the present disclosure.

Referring to FIG. 4, a block diagram of the interior of an augmented reality with real-time interactive analysis system 10 according to an embodiment of the present disclosure is shown. Similarly, the augmented reality with real-time interactive analysis system 10 can be installed in the portable electronic device 1. The portable electronic device 1 is disposed with a display screen 2, and interacts with a checklist 100. The checklist 100 includes a plurality of basic data fields and a plurality of biochemical fields. The augmented reality with real-time interactive analysis system 10 of the present disclosure includes an image reading identification processing module 11, a data identification converting module 20, a database 21, a health information controller 22, an augmented reality image corresponding module 26, and a visual feedback generating unit 28. The output of the health information controller 22 includes a plurality of health signals 24, and the plurality of health signals 24 are transmitted to the augmented reality image corresponding module 26.

The image reading identification processing module 11 shown in FIG. 4 is the block demonstrated by dotted lines, and is configured to read the image of the checklist 100 and identify the plurality of basic data fields and the data in the plurality of biochemical fields. The data identification converting module 20 is connected to the image reading identification processing module 11, and is configured to convert the plurality of basic data fields and the data in the plurality of biochemical fields of the checklist 100 into identifiable digital data to which is employed by the health information controller 22 for the follow-up process. The health information controller 22 is connected to the data identification converting module 20 and the image reading identification processing module 11, and is configured to produce the plurality of health signals 24 according to the plurality of basic data fields and the data in the plurality of biochemical fields. The database 21 is connected to the health information controller 22, and is installed with a plurality of preset standard values, in which each of the preset standard values is set correspondingly to an item of each of the plurality of biochemical fields. The augmented reality image corresponding module 26 is connected to the health information controller 22, and is configured to receive the plurality of health signals 24 and produce an augmented reality checklist image 101 corresponding to the checklist 100. As shown in FIG. 5, the augmented reality checklist image 101 is a signal field corresponding to each of the plurality of biochemical fields. That is, on the checklist 100 or a personal health checklist, a biochemical checklist, and so on, each added field (i.e. the signal field) is made at the lateral end of each of the corresponding biochemical fields in the augmented reality image, and each addition is displayed at the end of each of the corresponding biochemical fields. The visual feedback generating unit 28 is connected to the augmented reality image corresponding module 26, and is configured to transmit the augmented reality checklist image 101 to the display screen 2.

In the augmented reality with real-time interactive analysis system 10, the health information controller 22 is configured to determine whether the data of each of the plurality of biochemical fields meets a preset standard value. If the data of each of the plurality of biochemical fields meets a preset standard value, a first signal is produced (a green light (G), in practice); if the data of each of the plurality of biochemical fields does not meet a preset standard value, a second signal is produced (a red light (R), in practice), and the first signal or the second signal corresponding to the plurality of biochemical fields is displayed in the signal field. Similarly, the preset standard value can be a preset standard interval. If the data of each of the plurality of biochemical fields is between the preset standard interval, the health information controller 22 produces a first signal, if the data of each of the plurality of biochemical fields exceeds the preset standard interval, the health information controller 22 produces a second signal, if the data of each of the plurality of biochemical fields falls behind the preset standard interval, the health information controller 22 produces a third signal, and the first signal, the second signal and the third signal are respectively displayed in the signal field.

In addition, in an exemplary embodiment, by means of the augmented reality with real-time interactive analysis system 10 of the present disclosure, when the health information controller 22 is determining whether the data of each of the plurality of biochemical fields meets the preset standard value, the health information controller 22 further obtains a biochemical field from each of the plurality of biochemical fields which does not mostly comply with the preset standard value based on the operational aspect of the portable electronic device 1, and the augmented reality image corresponding module 26 produces the augmented reality image of a doll and a dialog box 102 on the display screen 2 as shown in FIG. 6.

In another exemplary embodiment, the checklist 100 of the present disclosure is installed with a QR code (not shown in the figures), and the QR code stores the plurality of basic data fields and the data in the plurality of biochemical fields. The image reading identification processing module 11 reads the image of the checklist 100 and identifies the QR code, and further identifies the plurality of basic data fields and the data in the plurality of biochemical fields. After that, the data identification converting module 20 converts the plurality of basic data fields and the data in the plurality of biochemical fields into digital data which is identifiable to the health information controller 22.

Reference is made to FIG. 4. The image reading identification processing module 11 shown in FIG. 4 further includes an image reading module 12, a field identification unit 14, a basic data processing module 16, and a biochemical field processing module 18. The portable electronic device 1 uses the image reading module 12 to read the image of the checklist 100. The field identification unit 14 is connected to the image reading module 12, and is configured to identify and distinguish each field of the checklist 100. The biochemical field processing module 18 is connected to the field identification unit 14, and is configured to identify the data in the plurality of biochemical fields. The function and connection of the data identification converting module 20, the health information controller 22, the database 21, the plurality of health signals 24, the augmented reality image corresponding module 26 and the visual feedback generating unit 28 shown in FIG. 4 are the same as that applied to the augmented reality with real-time interactive analysis system 10.

Furthermore, in practical application, the checklist of the present disclosure includes an images checklist, a table checklist, a strip checklist, or a checklist presented in other types.

In summary, the present disclosure provides an augmented reality with real-time interactive analysis method and a system thereof which are applicable to various portable electronic devices such as a smart phone, a tablet, and so on. By virtue of the present disclosure, the user can read a health checklist or a biochemical checklist in an animated and interactive manner. In addition, the present disclosure can effectively stimulate users to use applications installed in the smart handheld device and overcome the drawbacks associated with conventional checklists.

The above-mentioned descriptions represent merely the exemplary embodiment of the present disclosure, without any intention to limit the scope of the present disclosure thereto. Various equivalent changes, alterations or modifications based on the claims of the present disclosure are all consequently viewed as being embraced by the scope of the present disclosure.

What is claimed is:

1. An augmented reality with real-time interactive analysis method applicable to a portable electronic device, wherein the augmented reality with real-time interactive analysis method is an application installed in the portable electronic device, and wherein the portable electronic device comprises a display screen, the application interacts with a checklist, and wherein the checklist comprises a plurality of basic data fields and a plurality of biochemical fields; the augmented reality with real-time interactive analysis method comprising the steps of:

starting the application from the portable electronic device by a user; reading the checklist by the application;

identifying the plurality of basic data fields of the checklist and the plurality of biochemical fields of the checklist;

recording the plurality of basic data fields and data in the plurality of biochemical fields and converting the plurality of basic data fields and data in the plurality of biochemical fields into digital data;

determining whether the data of each of the plurality of biochemical fields meets a preset standard value, and wherein each biochemical field corresponds to the preset standard value;

the application producing a first signal or a second signal corresponding to whether results conform to the preset standard values;

the application generating an augmented reality checklist image on the display screen and adding a signal field to each of the plurality of biochemical fields; and the application further obtaining a biochemical field from each of the plurality of biochemical fields which does not mostly comply with the preset standard value, and the application producing an augmented reality image of a doll and a dialog box on the display screen, wherein the augmented reality image of a doll and a dialog box covers partially the augmented reality checklist image, and the content of the augmented reality image of a doll and a dialog box is suggestions and prompting associated with the data in the biochemical field which does not mostly comply with the preset standard value;

displaying the first signal or the second signal corresponding to the plurality of biochemical fields in the signal field;

wherein each of the preset standard values is pre-stored in the application.

2. The augmented reality with real-time interactive analysis method according to claim 1, wherein each of the preset standard values is a preset standard interval; and wherein if the data of each of the plurality of biochemical fields is between the preset standard interval, the first signal is produced; if the data of each of the plurality of biochemical fields exceeds the preset standard interval, the second signal is produced; if the data of each of the plurality of biochemical fields falls behind the preset standard interval, a third signal is produced; and the first signal, the second signal and the third signal are respectively displayed in the signal field.

3. The augmented reality with real-time interactive analysis method according to claim 1, wherein the checklist includes an images checklist, a table checklist or a strip checklist.

4. An augmented reality with real-time interactive analysis method applicable to a portable electronic device, wherein the augmented reality with real-time interactive analysis method is an application installed in the portable electronic device, and wherein the portable electronic device comprises a display screen, the application interacts with a checklist, and wherein the checklist comprises a plurality of basic data fields and a plurality of biochemical fields; the augmented reality with real-time interactive analysis method comprising the steps of:

starting the application from the portable electronic device by a user; reading the checklist by the application;

identifying the plurality of basic data fields of the checklist and the plurality of biochemical fields of the checklist;

recording the plurality of basic data fields and data in the plurality of biochemical fields and converting the plurality of basic data fields and data in the plurality of biochemical fields into digital data;

determining whether the data of each of the plurality of biochemical fields meets a preset standard value, and wherein each biochemical field corresponds to the preset standard value;

obtaining a biochemical field from each of the plurality of biochemical fields which does not mostly comply with the preset standard value according to whether results conform to the preset standard values; and generating an augmented reality checklist image on the display screen, and displaying an augmented reality image of a doll and a dialog box on the display screen, wherein the augmented reality image of a doll and a dialog box covers partially the augmented reality checklist image, and the content of the augmented reality image of a doll and a dialog box is suggestions and prompting associated with the data in the biochemical field which does not mostly comply with the preset standard value;

wherein each of the preset standard values is pre-stored in the application.

5. An augmented reality with real-time interactive analysis system installed in a portable electronic device and using an augmented reality with real-time interactive analysis method, wherein the portable electronic device is disposed with a display screen and interacts with a checklist, and wherein the checklist comprises a plurality of basic data fields and a plurality of biochemical fields; the augmented reality with real-time interactive analysis system comprising:
- an image reading identification processing module configured to read the image of the checklist and identify the plurality of basic data fields and the data in the plurality of biochemical fields;
- a data identification converting module connected to the image reading identification processing module, and configured to convert the plurality of basic data fields and the data in the plurality of biochemical fields of the checklist into identifiable digital data;
- a health information controller connected to the data identification converting module and the image reading identification processing module, and configured to produce a plurality of health signals according to the plurality of basic data fields and the data in the plurality of biochemical fields;
- a database connected to the health information controller, and installed with a plurality of preset standard values, wherein each of the preset standard values is set correspondingly to an item of each of the plurality of biochemical fields;
- an augmented reality image corresponding module connected to the health information controller, and configured to receive the plurality of health signals and produce an augmented reality checklist image corresponding to the checklist, wherein the augmented reality checklist image is the image of a signal field produced correspondingly to each of the plurality of biochemical fields; and
- a visual feedback generating unit connected to the augmented reality image corresponding module, and configured to transmit the augmented reality checklist image to the display screen, wherein the augmented reality checklist image is generated on the display screen;
- wherein the health information controller is configured to determine whether the data of each of the plurality of biochemical fields meets a preset standard value; if the data of each of the plurality of biochemical fields meets a preset standard value, a first signal is produced; if the data of each of the plurality of biochemical fields does not meet a preset standard value, a second signal is produced, and the first signal or the second signal corresponding to the plurality of biochemical fields is displayed in the signal field, and
- wherein when the health information controller is determining whether the data of each of the plurality of biochemical fields meets the preset standard value, the health information controller further obtains a biochemical field from each of the plurality of biochemical fields which does not mostly comply with the preset standard value, and the augmented reality image corresponding module displays the augmented reality image of a doll and a dialog box on the display screen, wherein the augmented reality image of a doll and a dialog box covers partially the augmented reality checklist image, and the content of the augmented reality image of a doll and a dialog box is suggestions and prompting associated with the data in the biochemical field which does not mostly comply with the preset standard value.

6. The augmented reality with real-time interactive analysis system according to claim 5, wherein the health information controller is configured to determine whether the data of each of the plurality of biochemical fields meets the preset standard value, and the preset standard value is a preset standard interval; and wherein if the data of each of the plurality of biochemical fields is between the preset standard interval, the health information controller produces a first signal, if the data of each of the plurality of biochemical fields exceeds the preset standard interval, the health information controller produces a second signal, if the data of each of the plurality of biochemical fields falls behind the preset standard interval, the health information controller produces a third signal, and the first signal, the second signal and the third signal are respectively displayed in the signal field.

7. The augmented reality with real-time interactive analysis system according to claim 5, wherein the checklist is installed with a QR code, the QR code stores the plurality of basic data fields and the data in the plurality of biochemical fields; and wherein the image reading identification processing module reads the image of the checklist and identifies the QR code, and further identifies the plurality of basic data fields and the data in the plurality of biochemical fields; and wherein the data identification converting module converts the plurality of basic data fields and the data in the plurality of biochemical fields into digital data which is identifiable toward the health information controller.

8. The augmented reality with real-time interactive analysis system according to claim 5, wherein the checklist includes an images checklist, a table checklist or a strip checklist.

9. An augmented reality with real-time interactive analysis system installed in a portable electronic device and using an augmented reality with real-time interactive analysis method, wherein the portable electronic device is disposed with a display screen and interacts with a checklist, and wherein the checklist comprises a plurality of basic data fields and a plurality of biochemical fields; the augmented reality with real-time interactive analysis system comprising:
- an image reading module configured to read the image of the checklist;
- a field identification unit connected to the image reading module, and configured to identify and distinguish each field of the checklist;
- a basic data processing module connected to the field identification unit, and configured to identify the data of each of the plurality of biochemical fields;
- a biochemical field processing module connected to the field identification unit, and configured to identify the data in the plurality of biochemical fields;
- a data identification converting module connected to the image reading identification processing module, and configured to convert the plurality of basic data fields and the data in the plurality of biochemical fields of the checklist into identifiable digital data;
- a health information controller connected to the data identification converting module and the image reading identification processing module, and configured to produce a plurality of health signals according to the plurality of basic data fields and the data in the plurality of biochemical fields;
- a database connected to the health information controller, and installed with a plurality of preset standard intervals, wherein each of the preset standard intervals is set correspondingly to an item of each of the plurality of biochemical fields;
- an augmented reality image corresponding module connected to the health information controller, and configured to receive the plurality of health signals and produce an augmented reality checklist image corresponding to the checklist; wherein the augmented reality checklist image is the image of a signal field produced correspondingly to each of the plurality of biochemical fields; and a visual feedback generating unit connected to the augmented reality image corresponding module, and configured to transmit the augmented reality checklist image to the display screen, wherein the augmented reality checklist image is generated on the display screen;

wherein the health information controller is configured to determine whether the data of each of the plurality of biochemical fields meets a preset standard interval; wherein if the data of each of the plurality of biochemical fields is between the preset standard interval, the health information controller produces a first signal, if the data of each of the plurality of biochemical fields exceeds the preset standard interval, the health information controller produces a second signal, if the data of each of the plurality of biochemical fields falls behind the preset standard interval, the health information controller produces a third signal, and the first signal, the second signal and the third signal are respectively displayed in the signal field, wherein when the health information controller is determining whether the data of each of the plurality of biochemical fields meets the preset standard value, the health information controller further obtains a biochemical field from each of the plurality of biochemical fields which does not mostly comply with the preset standard value, and the augmented reality image corresponding module displays the augmented reality image of a doll and a dialog box on the display screen, wherein the augmented reality image of a doll and a dialog box covers partially the augmented reality checklist image, and the content of the augmented reality image of a doll and a dialog box is suggestions and prompting associated with the data in the biochemical field which does not mostly comply with the preset standard value.

\* \* \* \* \*